United States Patent [19]

Goodbrand et al.

[11] Patent Number: 5,723,671

[45] Date of Patent: Mar. 3, 1998

[54] ARYLAMINE PROCESSES

[75] Inventors: H. Bruce Goodbrand, Hamilton; Nan-Xing Hu, Oakville; Beng S. Ong, Mississauga, all of Canada

[73] Assignee: Xerox Corporation, Stamford, Conn.

[21] Appl. No.: 790,669

[22] Filed: Jan. 30, 1997

[51] Int. Cl.⁶ .................................................. C07C 209/10
[52] U.S. Cl. .......................... 564/405; 564/307; 564/395; 564/433; 564/435
[58] Field of Search .................................. 564/307, 405, 564/435, 433, 395

[56] References Cited

U.S. PATENT DOCUMENTS

| | | | |
|---|---|---|---|
| 4,240,987 | 12/1980 | Martin et al. | 570/206 |
| 4,265,990 | 5/1981 | Stolka et al. | 430/59 |
| 4,299,983 | 11/1981 | Martin et al. | 564/394 |
| 4,485,260 | 11/1984 | Szabo et al. | 564/402 |
| 4,764,625 | 8/1988 | Turner et al. | 548/442 |
| 4,801,517 | 1/1989 | Frechet et al. | 430/59 |
| 5,495,049 | 2/1996 | Nukada et al. | 564/433 |

FOREIGN PATENT DOCUMENTS 0617005  3/1993  European Pat. Off. .

*Primary Examiner*—Brian M. Burn
*Attorney, Agent, or Firm*—E. O. Palazzo

[57] ABSTRACT

A process for the preparation of N,N-bis(3,4-dimethylphenyl)-4-biphenylamine which comprises the reaction of an aminobiphenyl and an iodoxylene in the presence of a ligand copper catalyst, and wherein the ligand is selected from the group consisting of monodentate tertiary amines and bidentate tertiary amines, and which reaction is accomplished at a temperature of from about 120° C. to about 150° C.

27 Claims, No Drawings

ARYLAMINE PROCESSES

PENDING APPLICATIONS AND PATENTS

Disclosed in U.S. Pat. No. 5,648,842, U.S. Pat. No. 5,654,482, and U.S. Pat. No. 5,648,538, the disclosures of each application being totally incorporated herein by reference, are generally processes for the preparation of arylamines. For example, in U.S. Pat. No. 5,648,842 and U.S. Pat. No. 5,654,482, respectively, there is disclosed a process for the preparation of triarylamines which comprises the reaction of an aniline and a haloaromatic component in the presence of a ligated copper catalyst, and wherein the ligand is selected from the group consisting of monodentate tertiary amines and bidentate tertiary amines, and which reaction is accomplished at a temperature of from about 120° C. to about 150° C., and an Ullmann condensation process for the preparation of triarylamines which comprises the reaction of an aniline and a halobenzene in the presence of an organic solvent, an alkali metal hydroxide, a ligated copper catalyst, and wherein the ligand is selected from the group consisting of monodentate tertiary amines and bidentate tertiary amines, and which reaction is accomplished at a temperature of from about 120° to about 135° C.

Also, disclosed in copending applications U.S. Ser. No. 08/791,694, and U.S. Ser. No. 08/791,694, filed concurrently herewith, and the disclosures of which are totally incorporated herein by reference, are processes for the preparation of aryl amines, and more specifically, a process for the preparation of N,N-bis(3,4-dimethylphenyl)-4-biphenylamine, which comprises the reaction of N,N-bis(3,4-dimethylphenyl)amine and an iodobiphenyl in the presence of a ligand copper catalyst, and wherein the ligand is selected from the group consisting of monodentate tertiary amines and bidentate tertiary amines, and which reaction is accomplished at a temperature of from about 120° C. to about 150° C.; and a process for the preparation of N,N-bis(3,4-dimethylphenyl)-4-biphenylamine, which comprises the reaction of N-(3,4-dimethylphenyl)-4-biphenylamine and an iodoxylene in the presence of a ligated copper catalyst, and wherein the ligand is selected from the group consisting of monodentate tertiary amines and bidentate tertiary amines, and which reaction is accomplished at a temperature of from about 120° C. to about 150° C.

BACKGROUND OF THE INVENTION

This invention is generally directed to processes for the preparation of arylamines, useful for photoconductive imaging members, and more specifically, the present invention relates to the preparation of N,N-bis(3,4-dimethylphenyl)-4-biphenylamine. In embodiments, the present invention relates to an improved process for the preparation of hole transporting molecules, such as arylamines, and wherein there are selected certain copper catalysts, and in embodiments low temperatures. The catalysts selected for the processes of the present invention include ligated copper salts, and more specifically, copper (1) salts, and wherein the ligands are characterized as monodentate tertiary amines and bidentate tertiary amines, such as 1,10-phenanthroline or pyridine, and the like. The products obtained, such as N,N-bis(3,4-dimethylphenyl)-4-biphenylamine, with the processes of the present invention can be incorporated into layered photoconductive imaging members with a photogenerating layer, a charge transport layer, and a supporting substrate, reference for example U.S. Pat. No. 4,265,990, the disclosure of which is totally incorporated herein by reference. The aforementioned layered photoconductive imaging members can be negatively charged when the photogenerating layer is situated between the charge transport layer and the substrate, or positively charged when the charge transport layer is situated between the photogenerating layer and the supporting substrate. The layered photoconductive imaging members can be selected for a number of different known imaging and printing processes including, for example, electrophotographic imaging processes, especially xerographic imaging and printing processes wherein negatively charged or positively charged images are rendered visible with toner compositions of the appropriate charge, and for digital processes. Generally, the imaging members are sensitive in the wavelength regions of from about 500 to about 850 nanometers, thus diode lasers can be selected as the light source.

PRIOR ART

Processes for the preparation of certain charge transporting molecules are known, reference for example U.S. Pat. Nos. 4,299,983; 4,485,260; 4,240,987; 4,764,625 and 4,299,983, the disclosures of each of these patents being totally incorporated herein by reference. These and other prior art illustrate the Ullmann condensation of 3-methyldiphenylamine and diiodobiphenyl at high temperatures, for example 160° C., reference the U.S. Pat. No. 4,764,625, and wherein nonligand cuprous oxide catalysts are selected. With these processes, the crude charge transport molecules generated are of lower quality and possess lower purity than the charge transport molecules obtained with the processes of the present invention. Higher crude purities enable a much wider choice of purification protocols. Also, high temperature reactions are more prone to produce troublesome impurities necessitating extensive purification. This becomes particularly important when products with electronic grade purities are required, such as for use as charge transporting molecules in layered photoconductive xerographic imaging members, reference U.S. Pat. No. 4,265,990, the disclosure of which is totally incorporated herein by reference. Moreover, lower temperatures have a positive influence on the economics of these processes primarily because of reduced energy demands.

European patent publication EP 0 617 005 A2 discloses certain arylamines, and more specifically, triacrylamines of formula (I), which can be prepared by acetylating 3,4-xylidene, thereafter condensing the acetylated product with a halogenated aryl compound to form N-(3,4-dimethylphenyl)-N-arylamine, and then condensing the diarylamine compound with a certain halogenated aryl compound of the formula $Ar_2X$, see for example page 4 of this patent publication, and wherein a certain copper catalyst of a metallic copper powder, copper sulfate, cuprous oxide, copper iodide, or copper nitrate is selected, see page 4, beginning at line 46. This publication also indicates that the condensation temperature is high, 200° C., and the reaction can consume substantial time, for example 30 hours. Long reaction times at high temperature are apparently required for the processes of the above mentioned EPO patent publication to secure the desired product. In contrast, with the present invention there is provided in embodiments thereof a process for the preparation of bis(3,4-dimethylphenyl)-4-biphenylamine under substantially milder conditions, and wherein ligand catalysts are selected. Furthermore, with the present invention in embodiments there are provided with the copper ligand catalysts selected shorter reaction times for the synthesis of the amine product, and wherein the desired product is of high purity, for example 95 percent pure, and which product can be easily further purified to an electronic grade of about 99.7 percent pure or greater.

SUMMARY OF THE INVENTION

Examples of objects of the present invention include in embodiments the following.

It is an object of the present invention to provide processes for the preparation of charge transport arylamines with many of the advantages illustrated herein, and wherein the charge transporting, especially hole transporting, components resulting can be selected for layered photoconductive imaging members.

It is yet another object of the present invention to provide low temperature processes for the preparation of charge transport components, especially N,N-bis(3,4-dimethylphenyl)-4-biphenylamine.

Another object of the present invention resides in the preparation of charge transport components by the Ullmann condensation reaction, and wherein organic ligands of copper are selected as catalyst adjuvants, or catalyst accelerators.

It is another object of the present invention to synthesize in one step bis(3,4-dimethylphenyl)-4-biphenylamine under substantially mild conditions from commercially available materials.

Furthermore, it is an object of the present invention to provide a product in a high state of purity enabling it to be readily further purified if needed to electronic grade purity.

Further, in another object of the present invention there are provided economically scaleable processes for the preparation of arylamines, especially N,N-bis(3,4-dimethylphenyl)-4-biphenylamine in high purity and in excellent yields.

Another object of the present invention relates to processes wherein there can be selected lower temperatures of from about 100° C. to about 150° C. (Centigrade), and preferably from about 120° C. to about 130° C., and wherein organic ligands of copper are selected as a catalyst accelerator, and wherein the crude product obtained is of excellent purity, and which product may be further purified by known methods, such as filtration, distillation, column chromatography, vacuum distillation, and the like.

A further object of the present invention resides in the provision of photoresponsive imaging members with an arylamine hole transport layer containing hole transport components comprised of N,N-bis(3,4-dimethylphenyl)-4-biphenylamine obtained by the processes illustrated herein, and a photogenerator layer.

Moreover, in another object of the present invention there are provided processes for the preparation of hole transporting molecules wherein the temperature of the reaction can be lower than the about 160° to 220° C. utilized for the preparation of certain commercial hole transporting arylamines, and more specifically, wherein the invention reaction in embodiments can be accomplished, for example, at temperatures 75° C. lower than 200° C., and yet more specifically at 125° C.; and also wherein novel catalysts, such as the product of cuprous chloride, and a 1,10-phenanthroline chelating agent is selected. The aforementioned lower temperature, and milder reaction conditions enable, it is believed, simpler processes, and more efficient protocols for the preparation of pure, that is for example electronic grade, arylamines of N,N-bis(3,4-dimethylphenyl)-4-biphenylamine.

Further, in another object of the present invention in embodiments thereof there may be enabled, it is believed, processes for the preparation of oligomers, polymers, intermediates, and the like.

The present invention relates to processes for the preparation of arylamines, and more specifically, processes for the preparation of N,N-bis( 3,4-dimethylphenyl)-4-biphenylamines, and which amines can be selected as charge transport molecules in layered photoconductive imaging members, reference U.S. Pat. No. 4,764,625, the disclosure of which is totally incorporated herein by reference. The process in embodiments of the present invention comprises the reaction of an appropriate amine, such as 4-aminobiphenyl with an iodobenzene, especially 4-iodo-ortho-xylene in the presence of a ligated copper catalyst, and wherein the ligand is selected from the group consisting of monodentate tertiary amines and bidentate tertiary amines.

Disclosed is a process for the preparation of N,N-bis(3, 4-dimethylphenyl)-4-biphenylamine, which comprises the reaction of an aminobiphenyl and an iodoxylene, in the presence of a ligand copper catalyst, and wherein the ligand is selected from the group consisting of monodentate tertiary amines and bidentate tertiary amines, and which reaction is accomplished at a temperature of from about 120° C. to about 150° C.; a process wherein the aminobiphenyl is 4-aminobiphenyl, and the iodoxylene is 4-iodo-ortho-xylene; wherein subsequent to heating, cooling is accomplished, and the N,N-bis(3,4-dimethylphenyl)-4-biphenylamine product is isolated; wherein the temperature is from about 120° C. to about 140° C.; wherein the temperature is about 120° C.; wherein from about 0.01 to about 0.1 equivalent of the ligated copper catalyst are selected, the amount of 4-aminobiphenyl selected is about 1 equivalent and the amount of 4-iodo-ortho-xylene selected is from about 2 to about 3 equivalents; wherein the reaction is accomplished in the presence of a known hydrocarbon solvent of, for example, tridecane, toluene or xylene, and the like; wherein the copper is copper (1); wherein the ligand is selected from the group consisting of 1,10-phenanthrolinepyridine and pyridine; wherein the 4-aminobiphenyl is of the formula

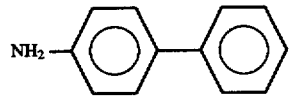

wherein the N,N-bis(3,4-dimethylphenyl)-N-(4-biphenyl) amine is of the formula

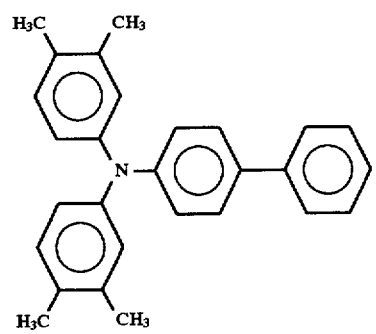

wherein the 4-iodo-ortho-xylene is of the formula

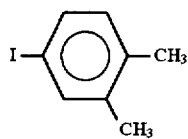

wherein the temperature is from about 120° C. to about 130° C.; wherein subsequent to heating, rapid cooling is accomplished, and the N,N-bis(3,4-dimethylphenyl)-4-biphenylamine product is isolated; a process for the preparation of N,N-bis(3,4-dimethylphenyl)-N-(4-biphenyl)amine which comprises the reaction of 4-aminobiphenyl, and 4-iodo-ortho-xylene in the presence of a ligand copper catalyst, and wherein the ligand is selected from the group consisting of monodentate tertiary amines and bidentate tertiary amines, and which reaction is accomplished at a temperature of from about 120° C. to about 150° C., followed by cooling and isolating the N,N-bis(3,4-dimethylphenyl)-N-(4-biphenyl)amine product; wherein the catalyst is selected from the group consisting of 1,10-phenanthrolato copper (1) (monovalent) chloride, dipyridino copper (1) chloride, 1,10-phenanthrolato copper (1) bromide, dipyridino copper (1) bromide, and 1,10-phenanthrolato copper (1) chloride; wherein the catalyst is of the alternative formulas

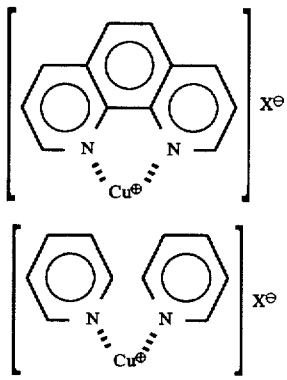

wherein X- is a halide; wherein the catalyst is of the alternative formulas

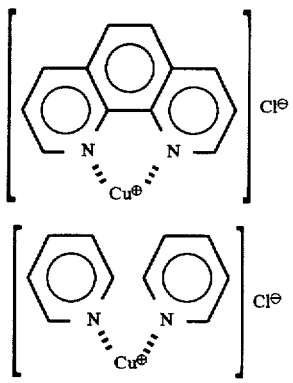

wherein the reaction of 4-aminobiphenyl and 4-iodo-ortho-xylene is accomplished by an Ullmann condensation; wherein the reaction time is from about 3 hours to about 6 hours; and/or a process for the preparation of N,N-bis(3,4-dimethylphenyl)-4-biphenylamine, which comprises the reaction of an aminobiphenyl and an iodoxylene, in the presence of a ligand copper catalyst, and wherein the ligand is selected from the group consisting of monodentate tertiary amines and bidentate tertiary amines.

In embodiments, the present invention relates to processes for the preparation of arylamines, and more specifically, processes for the preparation of N,N-bis(3,4-dimethylphenyl)-4-biphenylamines by the reaction of an aminobiphenyl, especially 4-aminobiphenyl and an iodoxylene, especially 4-iodo-o-xylene, and which reaction is accomplished in the presence of a ligated copper catalyst, and wherein the ligand is selected from the group consisting of monodentate tertiary amines and bidentate tertiary amines. The aforementioned reactions are accomplished at temperatures, for example, of from about 120° C. to about 150° C. (Centigrade), and preferably from about 120° C. to about 140° C., and more preferably at about 125° C., and wherein the catalyst is 1,10-phenanthrolato copper (1) (monovalent) chloride, dipyridino copper (1) chloride, 1,10-phenanthrolato copper (1) bromide, dipyridino copper (1) bromide, 1,10-phenanthrolato copper (1) chloride, 1,10-phenanthrolato copper (1) bromide, or dipyridino copper (1) bromide.

The catalyst selected is of importance and in embodiments is comprised of a copper (1) containing organic ligand, and wherein the ligand is selected from the group consisting of monodentate tertiary amines and bidentate tertiary amines as indicated herein, and more specifically, copper catalysts or compounds of the formulas (1,10-phenanthrolato)Cu(X), bis(pyridinato)Cu(X) wherein X is a halide, such as chloride.

The catalyst selected for the processes of the present invention is as illustrated herein, and in embodiments is comprised of ligated copper salts, including the halide salts, such as chloride, bromide, iodide, and fluoride, especially copper (1), and wherein the ligands are monodentate tertiary amines, or bidentate tertiary amines, such as 1,10-phenanthroline or pyridine. The amount of catalyst selected can vary, and generally, the catalyst is employed in effective amounts, such as from about 1 to about 20 mole percent of the reactants, and preferably from about 3 to about 10 mole percent of the limiting reactant. Examples of postulated formula structures for the copper catalysts are as illustrated in the copending applications mentioned herein and include

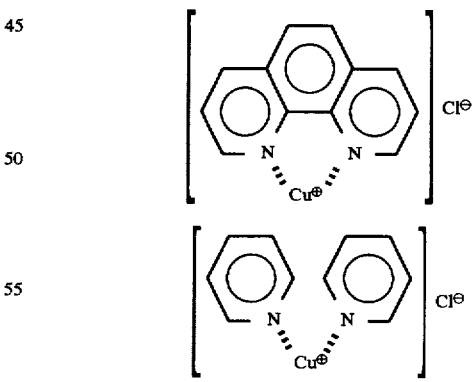

and in embodiments wherein the catalyst is 1,10-phenanthrolato copper (1) chloride, dipyridino copper (1) chloride, 1,10-phenanthrolato copper (1) bromide, or dipyridino copper (1) bromide, and the like. In the above formulas Cl can be replaced by X wherein X is a halogen, such as chloride, bromide, iodide, or fluoride.

The catalysts can be prepared as illustrated herein, in the copending applications mentioned herein, and more specifically, by the reaction of a copper salt like cuprous chloride with the appropriate ligand like 1,10-phenanthroline, and which reaction is accomplished with heating, for example, from about 70° C. to about 125° C. The reaction mixture is cooled and the product catalyst may, it is believed, be isolated by, for example, filtration. Preferably, the catalyst is prepared in situ, as illustrated herein.

Embodiments of the present invention include the synthesis of N,N-bis(3,4-dimethylphenyl)-4-biphenylamine as follows. In an appropriate flask equipped for mechanical stirring and fitted with an inert gas purge and Dean-Stark trap under a reflux condenser was placed in the following order: about 1 mole of 4-aminobiphenyl, about 1 to 1.5 moles, and preferably 1.25 moles of 4-iodo-ortho-xylene, about 0.01 to 0.1, and preferably about 0.05 mole of cuprous chloride, about 0.01 to 0.1 mole, and preferably about 0.05 mole of 1,10-phenanthroline, about 6 to 10 moles, and preferably about 8 moles of flake alkali hydroxide, such as potassium hydroxide, and about 600 milliliters of toluene solvent. The resulting mixture is then heated rapidly to reflux and retained at 130° C. until chromatographic analysis reveals the reaction to be complete. Normally, this requires 4 to 5 hours of reflux. The water of reaction is continuously removed by azeotropic distillation. On completion, the reaction mixture is allowed to cool to room temperature and it is partitioned between 2 liters of toluene and 1.5 liters of deionized water. The resulting layers can be separated and the organic phase dried by azeotropic distillation of water. The toluene solution can then be treated with 240 grams of Alcoa CG-20 alumina and 150 grams of Filtrol-24™, an acid-washed clay, to primarily remove any color. Filtration and evaporation of the solvent provides the desired product in excellent high yield.

The product, which can be identified by analytical methods, such as high performance liquid chromatography, possessed a high purity in embodiments as indicated herein and, more specifically, from about 97 to about 99 percent pure as determined by HPLC, that is high performance liquid chromography.

Numerous different layered photoresponsive imaging members containing the charge transporting amines generated with the process of the present invention can be provided. In embodiments, thus the layered photoresponsive imaging members are comprised of a supporting substrate, a charge transport layer containing an arylamine hole transport component, or molecules obtained with the process of the present invention, and situated therebetween a photogenerator layer comprised, for example, of phthalocyanines, hydroxygallium phthalocyanines, especially Type V, titanyl phthalocyanines, perylenes, especially BZP, selenium, especially trigonal selenium, selenium alloys, and the like, including other effective known photogenerating pigments. Also disclosed are positively charged layered photoresponsive, or photoconductive imaging members comprised of a supporting substrate, a charge transport layer, especially an arylamine hole transport layer, and as a top overcoating a photogenerating layer. Moreover, disclosed are negatively charged photoresponsive imaging members comprised of a supporting substrate, a thin adhesive layer, a photogenerator layer dispersed in a polymeric resinous binder, and as a top layer arylamine hole transporting molecules dispersed in a polymeric resinous binder, and which arylamine molecules are obtained with the processes of the present invention.

The photoresponsive imaging members can be prepared by a number of known methods, the process parameters, and the order of coating of the layers being dependent on the member desired. The imaging members suitable for positive charging can be prepared by reversing the order of deposition of photogenerator and hole transport layers. The photogenerating and charge transport layers of the imaging members can be coated as solutions or dispersions onto selective substrates by the use of a spray coater, dip coater, extrusion coater, roller coater, wire-bar coater, slot coater, doctor blade coater, gravure coater, and the like, and dried at from 40° C. to about 200° C. for from 10 minutes to several hours, and more specifically, about 5 hours under stationary conditions or in an air flow. The coating is accomplished to provide a final coating thickness of from 0.01 to about 30 microns after it has dried. The fabrication conditions for a given layer can be tailored to achieve optimum performance and cost in the final device. The imaging members are useful in xerographic imaging processes wherein, for example, when the pigment is a titanyl phthalocyanine pigment, it absorbs light of a wavelength of from about 600 nanometers to about 900 nanometers. In these known processes, electrostatic latent images are initially formed on the imaging member, followed by development, and thereafter, transferring and fixing the image to a suitable substrate, such as paper. Moreover, the imaging members can be selected for electronic printing processes with gallium arsenide light emitting diode (LED) arrays which typically function at wavelengths of from 660 to about 830 nanometers.

Substrate layers selected for the imaging members can be opaque or substantially transparent, and may comprise any suitable material having the requisite mechanical properties. Thus, the substrate may comprise a layer of insulating material including inorganic or organic polymeric materials, such as MYLAR® a commercially available polymer, MYLAR® containing titanium, a layer of an organic or inorganic material having a semiconductive surface layer, such as indium tin oxide, or aluminum arranged thereon, or a conductive material inclusive of aluminum, chromium, nickel, brass, or the like. The substrate may be flexible, seamless, or rigid and many have a number of many different configurations, such as for example a plate, a cylindrical drum, a scroll, an endless flexible belt, and the like. In one embodiment, the substrate is in the form of a seamless flexible belt. In some situations, it may be desirable to coat on the back of the substrate, particularly when the substrate is a flexible organic polymeric material, an anticurl layer, such as for example polycarbonate materials commercially available as MAKROLON®.

The thickness of the substrate layer depends on many factors, including economical considerations, thus this layer may be of substantial thickness, for example over 3,000 microns, or of minimum thickness providing there are no adverse effects on the system. In one embodiment, the thickness of this layer is from about 75 microns to about 300 microns.

Generally, the thickness of the photogenerator layer depends on a number of factors, including the thicknesses of the other layers and the amount of photogenerator material contained in this layer. Accordingly, this layer can be of a thickness of from about 0.05 micron to about 10 microns when the photogenerator composition layer is present in an amount of from about 5 percent to about 100 percent by volume. In one embodiment, this layer is of a thickness of from about 0.25 micron to about 1 micron when the photogenerator composition is present in this layer in an amount of 30 to 75 percent by volume. The maximum thickness of this layer in an embodiment is dependent primarily upon factors, such as photosensitivity, electrical properties and mechanical considerations. The charge generator layer can be obtained by dispersion coating the photogenerating pigment, and a binder resin with a suitable solvent, however, the binder may be omitted. The dispersion can be prepared by mixing and/or milling the photogenerating pigment in equipment such as paint shakers, ball mills, sand mills and attritors. Common grinding media, such as glass beads, steel balls or ceramic beads, may be used in this equipment. The binder resin may be selected from a number of known polymers such as poly(vinyl butyral), poly(vinyl carbazole), polyesters, polycarbonates, poly(vinyl chloride), polyacrylates and methacrylates, copolymers of vinyl chloride and vinyl acetate, phenoxy resins, polyurethanes, poly(vinyl alcohol), polyacrylonitrile, polystyrene, and the like. The solvents to dissolve these binders or resins depend upon the particular resin. In embodiments, it is desirable to select solvents that do not effect the other coated layers of the device. Examples of useful solvents are ketones, alcohols, aromatic hydrocarbons, halogenated aliphatic hydrocarbons, ethers, amines, amides esters, and the like. Specific solvent examples are cyclohexanone, acetone methyl ethyl ketone, methanol, ethanol, butanol, amyl alcohol, toluene xylene, chlorobenzene, carbon tetrachloride, chloroform, methylene chloride trichloroethylene, tetrahydrofuran, dioxane, diethyl ether dimethylformamide, dimethylacetamide, butyl acetate, ethyl acetate methoxyethyl acetate, and the like.

The coating of the photogenerating pigment dispersion can be accomplished with spray, dip or wire-bar methods such that the final dry thickness of the charge generator layer is from 0.01 to 30 microns and preferably from 0.1 to 15 microns after being dried at 40° C. to 150° C. for 5 to 90 minutes.

Illustrative examples of polymeric binder resinous materials that can be selected for the photogenerator pigment layer are as illustrated herein and include those polymers as disclosed in U.S. Pat. No. 3,121,006, the disclosure of which is totally incorporated herein by reference.

As adhesives usually in contact with the supporting substrate, there can be selected various known substances inclusive of polyesters, polyamides, poly(vinyl butyral), poly(vinyl alcohol), polyurethane and polyacrylonitrile. This layer is of a thickness of from about 0.05 micron to about 1 micron. Optionally, this layer may contain conductive and nonconductive particles, such as zinc oxide, titanium dioxide, silicon nitride, carbon black, and the like, to provide, for example, in embodiments of the present invention, desirable electrical and optical properties.

Examples of the highly insulating and transparent resinous inactive binders selected for the amine charge transport layer include components such as those described in U.S. Pat. No. 3,121,006, the disclosure of which is totally incorporated herein by reference. Specific examples of organic resinous materials include polycarbonates, acrylate polymers, vinyl polymers, cellulose polymers, polyesters, polysiloxanes, polyamides, polyurethanes and epoxies as well as block, random or alternating copolymers thereof. Preferred electrically inactive binders are comprised of polycarbonate resins having a molecular weight of from about 20,000 to about 100,000, with a molecular weight of from about 50,000 to about 100,000 being particularly preferred. Generally, the resinous binder contains from about 10 to about 75 percent by weight of the active charge transport material, and preferably from about 35 percent to about 50 percent of this material.

Also, disclosed are methods of imaging and printing with the photoresponsive devices illustrated herein. These methods generally involve the formation of an electrostatic latent image on the imaging member, followed by developing the image with a toner composition, reference U.S. Pat. Nos. 4,560,635; 4,298,697 and 4,338,390, the disclosures of which are totally incorporated herein by reference, subsequently transferring the image to a suitable substrate, and permanently affixing the image thereto. In those environments wherein the device is to be used in a printing mode, the imaging method involves the same steps with the exception that the exposure step can be accomplished with a laser device or image bar.

The following Examples are being supplied to further define various species of the present invention, it being noted that these Examples are intended to illustrate and not limit the scope of the present invention. Parts and percentages are by weight unless otherwise indicated. Yield and purity were determined by known analytical methods.

EXAMPLE I

Synthesis of N,N-bis(3,4-dimethylphenyl)-4-biphenylamine

In a 250 milliliter round-bottomed flask equipped with mechanical stirrer and fitted with a Dean-Stark trap under a reflux condenser were placed 8.46 grams (0.05 mole) of 4-aminobiphenyl, 25.53 grams (0.11 mole) of 4-iodo-ortho-xylene, 0.25 gram (0.0025 mole) of cuprous chloride, 0.45 gram (0.0025 mole) of 1,10-phenanthroline, 22.4 grams (0.4 mole) of flake potassium hydroxide and 30 milliliters of toluene solvent. The reaction was heated quickly to a reflux temperature of 130° C. and maintained at this temperature for 4 hours, after which time chromatographic analysis revealed the reaction to be complete. The reaction mixture was allowed to attain room temperature, about 25° C., and was partitioned between 200 milliliters of toluene and 150 milliliters of deionized water. The resulting organic layer was separated and water was removed by azeotropic distillation of water under a Dean-Stark trap. The product was decolorized by slurry treating the toluene solution with 36 grams of Filtrol-24™, an acid-washed clay, and 24 grams of Alcoa CG-20 alumina. After 3 hours stirring at reflux, the solution was cooled to room temperature and filtered. The product of N,N-bis(3,4-dimethylphenyl)-4-biphenylamine was recovered from the filtrate by evaporation of the solvent. Recrystallization from 40 milliliters of a one to one mixture of ethylacetate-isopropanol provided 13.2 grams (70 percent) of the above product. Chromatographic analysis by high performance liquid chromatography illustrated an excellent product purity of 99.8 percent and a melting temperature, which was determined by differential scanning calorimetry to be 113.21° C.

A number of hole transporting triarylamine compounds can be prepared in accordance with the present invention by repeating the above Example processes with different reactants, including different ligand catalysts and substantially similar results with, for example, regard to purity and yield can be obtained it is believed.

Other modifications of the present invention may occur to those of ordinary skill in the art subsequent to a review of the present application and these modifications, including equivalents thereof, are intended to be included within the scope of the present invention.

What is claimed is:

1. A process for the preparation of N,N-bis(3,4-dimethylphenyl)-4-biphenylamine which comprises the reaction of an aminobiphenyl and an iodoxylene in the presence of a ligand copper catalyst, and wherein the ligand is selected from the group consisting of monodentate tertiary amines and bidentate tertiary amines, and which reaction is accomplished at a temperature of from about 120° C. to about 150° C.

2. A process in accordance with claim 1 wherein the aminobiphenyl is 4-aminobiphenyl, and the iodoxylene is 4-iodo-orthoxylene.

3. A process in accordance with claim 1 wherein the heated reaction mixture is cooled, and the N,N-bis(3,4-dimethylphenyl)-4-biphenylamine product is isolated.

4. A process in accordance with claim 1 wherein the temperature is from about 120° C. to about 140° C.

5. A process in accordance with claim 1 wherein the temperature is about 120° C.

6. A process in accordance with claim 2 wherein from about 0.01 to about 0.1 molar equivalents of the ligated copper catalyst are selected, the amount of 4-aminobiphenyl selected is about 1 molar equivalent and the amount of 4-iodo-ortho-xylene selected is from about 2 to about 3 molar equivalents.

7. A process in accordance with claim 1 wherein the reaction is accomplished in the presence of a hydrocarbon solvent of tridecane, toluene or xylene.

8. A process in accordance with claim 1 wherein the copper is copper (1).

9. A process in accordance with claim 1 wherein said ligand is selected from the group consisting of 1,10-phenanthrolinepyridine and pyridine.

10. A process in accordance with claim 2 wherein the 4-aminobiphenyl is of the formula

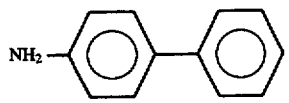

11. A process for the preparation of N,N-bis(3,4-dimethylphenyl)-4-biphenylamine which comprises the reaction of an aminobiphenyl and an iodoxylene in the presence of a ligand copper catalyst, and wherein the ligand is selected from the group consisting of monodentate tertiary amines and bidentate tertiary amines, and which reaction is accomplished at a temperature of from about 120° C. to about 150° C., and wherein the N,N-bis(3,4-dimethylphenyl)-N-(4-biphenyl)amine is of the formula

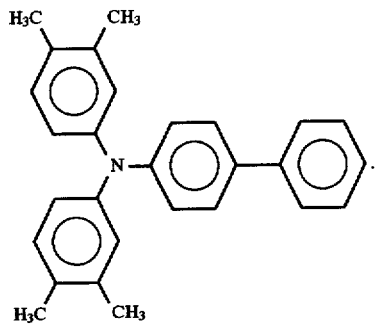

12. A process for the preparation of N,N-bis(3,4-dimethylphenyl)-4-biphenylamine which comprises the reaction of an aminobiphenyl and an iodoxylene in the presence of a ligand copper catalyst, and wherein the ligand is selected from the group consisting of monodentate tertiary amines and bidentate tertiary amines, and which reaction is accomplished at a temperature of from about 120° C. to about 150° C., and wherein the aminobiphenyl is 4-aminobiphenyl, and the iodoxylene is 4-iodo-ortho-xylene, and wherein the 4-iodo-orthoxylene is of the formula

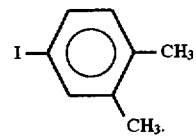

13. A process in accordance with claim 12 wherein the temperature is from about 120° C. to about 130° C.

14. A process in accordance with claim 2 wherein the heated reaction mixture is cooled, and the N,N-bis(3,4-dimethylphenyl)-4-biphenylamine product is isolated.

15. A process for the preparation of N,N-bis(3,4-dimethylphenyl)-N-(4-biphenyl)amine which comprises the reaction of 4-aminobiphenyl, and 4-iodo-ortho-xylene in the presence of a ligand copper catalyst, and wherein the ligand is selected from the group consisting of monodentate tertiary amines and bidentate tertiary amines, and which reaction is accomplished at a temperature of from about 120° C. to about 150° C., followed by cooling and isolating the N,N-bis(3,4-dimethylphenyl)-N-(4-biphenyl)amine product.

16. A process in accordance with claim 15 wherein the temperature is from about 120° C. to about 130° C.

17. A process in accordance with claim 1 wherein the catalyst is selected from the group consisting of 1,10-phenanthrolato copper (1) (monovalent) chloride, dipyridino copper (1) chloride, 1,10-phenanthrolato copper (1) bromide, dipyridino copper (1) bromide, and 1,10-phenanthrolato copper (1) chloride.

18. A process in accordance with claim 2 wherein the catalyst is selected from the group consisting of 1,10-phenanthrolato copper (1) (monovalent) chloride, dipyridino copper (1) chloride, 1,10-phenanthrolato copper (1) bromide, dipyridino copper (1) bromide, and 1,10-phenanthrolato copper (1) chloride.

19. A process in accordance with claim 15 wherein the catalyst is selected from the group consisting of 1,10-phenanthrolato copper (1) (monovalent) chloride, dipyridino copper (1) chloride, 1,10-phenanthrolato copper (1) bromide, dipyridino copper (1) bromide, and 1,10-phenanthrolato copper (1) chloride.

20. A process in accordance with claim 2 wherein said catalyst is of the alternative formulas

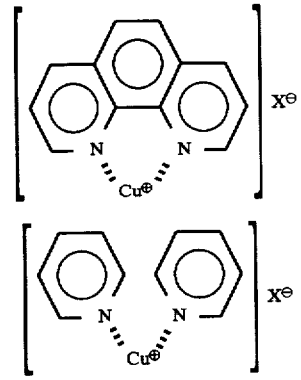

wherein X is a halide.

21. A process in accordance with claim 15 wherein said catalyst is of the alternative formulas

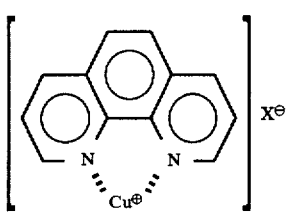

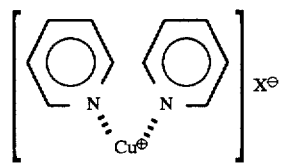

wherein X is a halide.

22. A process in accordance with claim 20 wherein X is chloride.

23. A process in accordance with claim 21 wherein X is chloride.

24. A process in accordance with claim 15 wherein the reaction of 4-aminobiphenyl and 4-iodo-ortho-xylene is accomplished by an Ullmann condensation.

25. A process in accordance with claim 1 wherein the reaction time is from about 3 hours to about 6 hours.

26. A process for the preparation of N,N-bis(3,4-dimethylphenyl)-4-biphenylamine which comprises the reaction of an aminobiphenyl and an iodoxylene, in the presence of a ligand copper catalyst, and wherein the ligand is selected from the group consisting of monodentate tertiary amines and bidentate tertiary amines.

27. A process in accordance with claim 26 wherein the catalyst is represented by one of the following alternative formulas

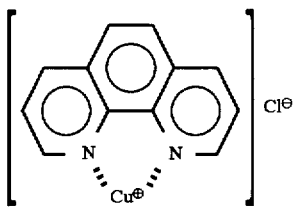

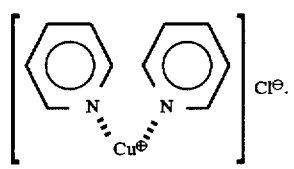

* * * * *